United States Patent
Grotewold

(10) Patent No.: US 6,709,867 B2
(45) Date of Patent: Mar. 23, 2004

(54) TRANSGENIC TURFGRASSES WHICH SIGNAL EXPOSURE TO CHEMICALS AND STRESS CONDITIONS

(75) Inventor: Erich Grotewold, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 131 days.

(21) Appl. No.: 10/044,300

(22) Filed: Oct. 26, 2001

(65) Prior Publication Data

US 2002/0188964 A1 Dec. 12, 2002

Related U.S. Application Data

(60) Provisional application No. 60/243,315, filed on Oct. 26, 2000.

(51) Int. Cl.$^7$ .................. C12N 15/82; C12N 15/90; C12N 15/84; A01H 5/00; A01H 5/10
(52) U.S. Cl. ................ 435/468; 435/320.1; 800/282; 800/298
(58) Field of Search .......................... 435/320.1, 410, 435/419, 468, 469, 470; 800/278, 282, 292, 295, 298

(56) References Cited

FOREIGN PATENT DOCUMENTS

WO    WO 96/22015    * 7/1996 ............ A01H/1/00

OTHER PUBLICATIONS

"Insertional Mutagenesis of the Maize P Gene by Intragenic Transposition of Ac" by Athma, et al., Genetics, 131:199–209 (May, 1992).
"Variation in the ability of the maize Lc regulatory gene to upregulate flavonoid biosynthesis in heterologous systems" by Bradley, et al., Plant Science, 140 (1999) 31–39.
"Newly Discovered Plant c–myb–Like Genes Rewrite the Evolution of the Plant mby Gene Family" by Braun, et al., Plant Physiology, Sep. 1999, vol. 121, pp. 21–24.
"Chapter Five: Transcription Factors and Metabolic Engineering: Novel Applications for Ancient Tools" by Braun, et al., Rec. Adv. Phyto., 2001, pp. 79–109.
"Fungal Zuotin Proteins Evolved from MIDA 1–like Factors by Lineage–Specific Loss of MYB Domains" by Braun, et al., Mol. Biol. Evol. 18(7): 1401–1412, 2001.
"Expression Profiling of the Maize Flavonoid Pathway Genes Controlled by Estradiol–Inducible Transcription Factors CRC and P" by Bruce, et al., The Plant Cell, vol. 12, 65–79, Jan. 2000.
"Functional Conservation of Plant Secondary Metabolic Enzymes Revealed by Complemantation of Arabidopsis Flavonoid Mutants with Maize Genes" by Dong, et al., Plant Physiology, Sep. 2001, vol. 127 pp. 46–57.
"Alternatively spliced products of the maize P gene encode proteins with homology tot he DNA–binding domain of myb–like transcription factors" by Grotewold, et al., Proc. Natl. Acad. Sci. USA, vol. 88, pp. 4587–4591, Jun. 1991.
"A possible hot spot for Ac insertion in the maize P gene " by Grotewold, et al., Mol Gen Genet, (1991) 230:329–331.
"Isolation and characterization of a maize gene encoding chalcone flavonone isomerase" by Grotewold, et al., Mol Gen Genet, (1994) 242:1–8.
"The myb–Homologous P Gene Controls Phlobaphene Pigmentation in Maize Floral Organs by Directly Activating Biosynthetic Gene Subset" by Grotewold, et al., Cell, vol. 76, 543–553, Feb. 11, 1994.
"Engineering Secondary Metabolism in Maize Cells by Ectopic Expression of Transcription Factors" by Grotewold, et al., The Plant Cell, Vo. 10, 721–740, May 1998.
"Identification of the residues in the Myb domain of maize Cl that specify the interaction with the bHLH cofactor R" by Grotewold, et al., PNAS, Dec. 5, 2000, vol. 97, No. 25, pp. 13579–13584.
"Subcellular trafficking of phytochemicals" by Grotewold, Recent Res. Devel. Plant Physiol., 2 (2001):31–48.
"Arabidopsis and Nicotiana Anthocyanin Production Activated by Maize Regulators R and Cl" by Lloyd, et al., Science, vol. 258, Dec. 11, 1992, pp. 1773–1775.
"A Regulatory Gene as a Novel Visible Marker for Maize Transformation" by Ludwig, et al., Science Jan. 26, 2000, vol. 247, pp. 449–450.
"Maize R2R3 Myb Genes: Sequence Analysis Reveals Amplification in the Higher Plants" by Rabinowicz, et al. Genetics, 153:427–444 (Sep. 1999).
"A novel reverse–genetic approach (SIMF) identifies Mutator insertions in Myb genes" by Rabinowicz, et al., Planta (2000) 211:887–893.
"Anthocyanin regulatory mutations in pea: effects on gene expression and complementation by R–like genes of maize" by Uimari et al., Mol Gen Genet (1998) 257: 198–204.
"Differences between Plant and Animal Myb Domains Are Fundamental for DNA Binding Activity, and Chimeric Myb Domains Have Novel DNA Binding Specificities" by Williams, et al., The Journal of Biological Chemistry, vol. 272, No. 1, Jan. 3, 1997, pp. 563–571.
"A Cytochrome $b_5$ is required for full activity of flavonoid 3 ,5 –hydroxylase, a cytochrome P45o involved in the formation of blue flower colors" by De Vetten, et al., Proc. Natl. Acad. Sci. USA, vol. 96, pp. 778–783, Jan. 1999.
"Evidence for Direct Activation of an Anthocyanin Promoter by the Maize Cl Protein and Comparison of DNA Binding by Related Myb Domain Proteins" by Sainz, et al., The Plant Cell, vol. 9, 611–625, Apr. 1997.
Joseph Mol, Erich Grotewold and Ronald Koes. How genes paint flowers and seeds. Page 212 Trendsin Plant Science Reviews. Jun. 1998, vol. 3, No. 6.

* cited by examiner

Primary Examiner—Ashwin Mehta
(74) Attorney, Agent, or Firm—Calfee, Halter & Griswold LLP

(57) ABSTRACT

Transgenic grass plants which exhibit a color different from the color exhibited by the corresponding non-transgenic grass plants under conditions of stress are provided Examples of such conditions include, but are not limited to, lack of fertilizer, lack of water, and attack by insects or pathogens. The genome of the transgenic grass plant comprises a transgene comprising a nucleic acid which encodes one or more regulators of anthocyanin biosynthesis, and an inducible promoter which is responsive to a stress condition, such as for example, nutrient deprivation, water deprivation, and attack by a pathogen.

20 Claims, No Drawings

TRANSGENIC TURFGRASSES WHICH SIGNAL EXPOSURE TO CHEMICALS AND STRESS CONDITIONS

CROSS REFERENCE TO RELATED APPLICATIONS

This invention claims priority to U.S. Provisional Patent Application Ser. No.: 60/243,315, filed Oct. 26, 2000.

The present invention was made, at least in part, with support from the National Science Foundation Grant No. MCB-9896111. The government has certain rights in the invention.

BACKGROUND

Attractive lawns are considered an asset by homeowners and owners of commercial recreational establishments, such as theme parks and golf courses. Typically, such lawns require treatment with a number of chemicals, including fertilizers, pesticides, and herbicides. Unfortunately, until the lawn begins to show obvious symptoms of a nutritional deficiency or infestation with weeds or pests, there is no way to determine when application of such chemicals is appropriate or warranted. Accordingly, there is often extensive and unnecessary usage of such compounds. Excessive treatment with these chemicals is expensive and environmentally compromising.

The maintenance of attractive lawns also requires application of water at appropriate times. If watering is delayed too long, leaf browning and leaf loss can occur. In addition, plants may die from draught stress. Watering too often can also result in plant damage. Moreover, frequent watering is expensive and poses serious problems in areas with water shortage.

Attempts have been made to overcome these problems by developing more resistant grasses that require less fertilizer, herbicides and pesticides. However, there currently are no systems available which permit application of fertilizers, pesticides and water to select areas that need such treatment. Accordingly, it is desirable to have grass plants which are capable of visually communicating their need for fertilizers, chemicals or water to the observer.

SUMMARY OF THE INVENTION

In one aspect, the present invention provides transgenic grass plants which exhibit a color different from the color exhibited by the corresponding non-transgenic grass plants under conditions of stress. Examples of such conditions include, but are not limited to, lack of fertilizer, lack of water, and attack by insects or pathogens. The genome of the present transgenic grass plant comprise a transgene comprising a nucleic acid which encodes one or more regulators of anthocyanin biosynthesis, hereinafter referred to as an "anthocyanin regulatory gene", and an inducible promoter which is responsive to a stress condition, such as for example, nutrient deprivation, water deprivation, and attack by a pathogen. The promoter, which is hereinafter referred to as a "stress" inducible promoter, is operably linked to the anthocyanin regulatory gene. Expression of the anthocyanin regulatory gene, in response to the stress condition, provides a gene product which activates expression of anthocyanin biosynthetic genes and results in the transgenic grass plant having a different color phenotype.

The present invention also relates to a construct and vector for preparing the transgenic grass. The construct and vector comprise a transgene comprising an anthocyanin regulatory gene operably linked to a stress inducible promoter.

The present invention also relates to a transgenic grass plant which constitutively exhibits a different color phenotype, particularly a red color phenotype. The genome the transgenic grass plant comprises a transgene comprising an exogenous anthocyanin regulatory gene operably linked to a constitutive promoter. Grass plants that constitutively display a colored phenotype are useful for display and decorative purposes.

The present invention also relates to methods of preparing the present transgenic grass plants and the seeds of the present transgenic grass plants.

DETAILED DESCRIPTION OF THE INVENTION

Definitions

Promoter, as used herein, refers to a recognition site on a DNA molecule that provide an expression control element for a gene and which allows the recruitment of RNA polymerase to initiate RNA synthesis (transcription) of the gene.

Regeneration, as used herein, refers to the process of growing a plant from a plant cell (e.g., plant protoplast, plant calli or plant explant).

Transformation, as used herein, refers to a process of introducing an exogenous DNA molecule (e g., a vector, a recombinant DNA molecule) into a cell, a callus, or protoplast in which that exogenous DNA is incorporated into a chromosome.

Transformed Cell, as used herein, refers to a cell whose DNA has been altered by the introduction of an exogenous DNA molecule into that cell.

Transgene, as used herein, refers to an exogenous gene which when introduced into the genome of a host cell through a process such as transformation, electroporation, particle bombardment, and the like, is expressed by the host cell and integrated into the cells genome such that the trait or traits produced by the expression of the transgene is inherited by the progeny of the transformed cell.

Transgenic Cell, as used herein, refers to any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic Plant, as used herein, refers to a plant or progeny thereof derived from a transformed plant cell or protoplast, wherein the plant DNA contains an introduced exogenous DNA molecule not originally present in a native, non-transgenic plant of the same strain.

Vector, as used herein, refers to a DNA molecule capable of replication in a host cell and/or to which another DNA segment can be operatively linked so as to bring about replication of the attached segment. A plasmid is an exemplary vector.

In one aspect, the present invention provides a nucleic acid construct comprising a transgene which comprises one or more anthocyanin regulatory genes and a stress inducible promoter which induces transcription of the anthocyanin regulatory gene in response to a stress condition. The promoter is operably linked to the anthocyanin regulatory gene or genes. The anthocyanin regulatory gene may be derived from a grass plant or from a plant other than grass. In one embodiment the, anthocyanin regulatory genes are derived from maize.

The present invention also provides a transgenic grass plant whose genome comprises a transgene comprising an exogenous anthocyanin regulatory gene and a promoter which is operably linked to the anthocyanin regulatory gene. In one embodiment, the promoter is a stress inducible promoter i.e., a promoter which induces expression of the anthocyanin regulatory gene in response to a stress condition such as for example, drought conditions, lack of fertilizer, or attack by a pathogen. In another embodiment, the promoter is a chemical inducible promoter, which induces expression of the anthocyanin regulatory gene in response to exposure of the plant to the chemical. In yet another embodiment, the promoter is a constitutive promoter which continuously drives expression of the anthocyanin regulatory gene.

Nucleic Acid Construct

A. Anthocyanin Regulatory and Biosynthetic Genes

Anthocyanins are non-toxic pigments that are responsible for many of the red and blue colors in plants. These pigments function to attract pollinating insects to plants and shield plant DNA from ultraviolet light damage. There are multiple anthocyanin genes producing pigments that cause plants to display different colors.

In corn or maize, anthocyanin biosynthesis requires expression of 20 or more genes. Some of these genes are anthocyanin biosynthetic genes; others are anthocyanin regulatory genes. An anthocyanin biosynthetic gene is a gene whose product is an enzyme that is involved in the biosynthesis of the anthocyanins. Examples of anthocyanin biosynthetic genes or loci in maize include C2, Whp, A1, CHI. A2, Bz1, and Bz2. In maize, there are at least 6 anthocyanin regulatory genes or loci, R, B, C1, P1, P and P, whose products are regulatory proteins which activate the transcription of one or more anthocyanin biosynthetic genes.

Although the genetic pathways for anthocyanin synthesis are complex, there is some understanding of regulation of anthocyanin synthesis. Two of the better understood protein factors known to activate expression of anthocyanin biosynthesis genes in maize are C1, which is a homologue of the mammalian transcription factor myb, and R, a group of factors that contain helix-loop-helix domains in their proteins. C1 and R proteins act together to increase expression of the anthocyanin biosynthesis genes by binding to their promoter regions and activating their transcription. Expressing the C1/R transcription factors in transgenic maize cell lines stimulates expression of genes of the anthocyanin biosynthetic pathway, resulting in the accumulation of the anthocyanins.

The R locus encompasses a gene family (in maize, located on chromosome 10) comprising at least three different genes; i.e., R (which itself may comprise duplicate genes organized in a tandem array), and the displaced duplicate genes R(Lc) and R(Sn). R typically conditions pigmentation of the aleurone (i.e., outer layer of a seed) but various alleles are known to confer distinct patterns of pigmentation. R(Lc) is associated with unique pigmentation of leaves and R(Sn) with unique pigmentation of the scutellar node. One state of R is associated with pigmentation of the whole plant (R(P)), while another is associated with pigmentation of the seeds (R(S)).

Alleles of the C1 locus of particular interest are C1 (Paz-Ares et. al., EMBO J. 6:3553–3558, 1987) and C1-S (Schleffer et. al., Mol.Gen.Genet. 242:40–48, 1994). Analysis of the sequences revealed the presence of two introns in the coding region of the gene. The protein encoded by the C1 and C1-S alleles shares homology with myb protooncogenes and is known to be a nuclear protein with DNA-binding capacity acting as a transcriptional activator.

In accordance with the present invention, applicants have shown that expression of exogenous C1/R transcription factors in grass plants activates expression of endogenous anthocyanin biosynthesis genes that are present in the genome of the grass plants but that are not normally expressed. As a result of the expression of the "normally-silent" endogenous anthocyanin biosynthesis genes, the transformed grass plants express a red color phenotype.

In one embodiment, the DNA construct of the present invention comprises a maize anthocyanin regulatory gene which, preferably, is selected from the group consisting of the R gene, the C1 gene, and combinations thereof. A construct which comprises both the R and C1 genes, herein called "C1/R", is described in articles by Grotewold et. al. (Cell 76: 543–553, 1994; Plant Cell 10:721–740, 1998), which are specifically incorporated herein by reference. The C1 and R genes encode proteins that interact with each other, bind to the promoters of anthocyanin structural genes and thereby activate transcription of the anthocyanin biosynthesis genes. The nucleotide sequence of various C1 and R, genes are available in Genbank and other references, such as for example, Paz-Ares et. al., EMBO J. 6:3553–3558, 1987. In another embodiment, the anthocyanin regulatory gene encodes a chimeric protein referred to hereinafter as the "CRC" protein. The CRC protein provides a convenient artificial single-gene regulator of anthocyanin accumulation. The CRC protein is formed by a translational fusion of the Myb domain of C1 (C), the complete R protein (R), followed by the C-terminal region of C1 (C).(see, Bruce, W. et al. (2000) Expression profiling of the maize flavonoid pathway genes controlled by estradiol-inducible transcription factors CFC and P. Plant Cell 12: 65–79).

B. Promoters

The transgene further comprises a promoter which is operably linked to the coding sequence of the anthocyanin regulatory gene for expression of the coding sequence. Preferably, the promoter is upstream of the anthocyanin regulatory gene or genes.

In one embodiment, the promoter is a stress inducible promoter that responds to a stress condition such as drought or infection with a pathogen. Promoters that respond to drought include the promoter of the maize rab28 gene as described in Pla et. al., Plant Mol. Biol. 21:259–266, 1993, the promoter of the maize rab17 gene as described in Busk et. al., Plant J. 11:1285–1295, 1997, and the promoter of the maize Ivr2 gene, as described in Pelleschi et. al., Plant Mol. Biol. 39:373–380, 1999. One example of a promoter that responds to pathogens is the promoter of the hydroxyproline-rich glycoprotein (Garcia-Muniz et. al., Plant Mol. Biol. 38:623–632, 1998).

In another embodiment, the promoter is a chemical inducible promoter that induces expression of the anthocyanin regulatory gene in response to contact of the transgenic plant with a chemical. Several promoters inducible by chemicals are available in plants (See, Gatz and Lenk I. (1998) Promoters that respond to chemical inducers. Trends Plant Sci. 3: 352–358). Suitable examples include, but are not limited to, steroid-inducible promoters (See, Lloyd et al. (1994) Epidermal cell fate determination in Arabadopsis: Patterns defined by a steroid inducible regulator. Science 266: 436–439.) and estradiol inducible promoters (See, Bruce, W. et al. (2000) Expression profiling of the maize flavonoid pathway genes controlled by estradiol-inducible transcription factors CFC and P. Plant Cell 12: 65–79).

In another embodiment, the promoter is a constitutive promoter such as for example, the 35S cauliflower mosaic virus (CaMV) promoter or a nopaline synthase or octopine synthase promoter. Examples of other constitutive promoters used in plants are the 19 S promoter, and promoters from genes encoding actin or ubiquitin. The promoters may be obtained from genomic DNA by using polymerase chain reaction (PCR), and then cloned into the construct. Standard recombinant DNA and molecular cloning techniques used here are well known in the art and are described by J. Sambrook, E. F. Fritsch and T. Maniatis, Molecular Cloning: A Laboratory Manual, Cold Spring Harbor Laboratory, Cold Spring Harbor, N.Y. (1989) and by T. J. Silhavy, M. L. Berman, and L. W. Enquist, Experiments with Gene Fusions, Cold Spring Harbor Laboratory, Cold Spring Harbor, N.Y. (1984).

In addition to the transgene, the DNA construct, preferably, also comprises other appropriate regulatory signals, such as a leader sequence, transcription terminator, and polyadenylation site. Such regulatory signals are readily available in the art.

C. Transcriptional Terminators

A variety of transcriptional terminators are available for use in expression cassettes. These are responsible for the termination of transcription beyond the transgene and its correct polyadenylation. Appropriate transcriptional terminators and those which are known to function in plants include the CaMV 35S terminator, the tml terminator, the nopaline synthase terminator and the pea rbcS E9 terminator.

D. Sequences for the Enhancement or Regulation of Expression

Numerous sequences have been found to enhance gene expression from within the transcriptional unit and these sequences can be used in conjunction with the genes of this invention to increase their expression in transgenic plants. Various intron sequences have been shown to enhance expression, particularly in monocotyledonous plants. For example, the introns of the maize Adh1 gene have been found to significantly enhance the expression of the wild-type gene under control of its cognate promoter when introduced into maize cells. Intron 1 was found to be particularly effective and enhanced expression in fusion constructs with the chloramphenicol acetyltransferase gene (Callis et. al., Genes Develop. 1:1183–1200, 1987). In the same experimental system, the intron from the maize bronze 1 gene had a similar effect in enhancing expression (Callis et al., supra). Intron sequences have been routinely incorporated into plant transformation vectors, typically within the non-translated leader.

A number of non-translated leader sequences, derived from viruses, are also known to enhance expression. Specifically, leader sequences from Tobacco Mosaic Virus (TMV, the "omegasequence"), Maize Chlorotic Mottle Virus (MCMV), and Alfalfa Mosaic Virus (AlMV) have been shown to be effective in enhancing expression (e.g., Gallie et. al., Nucl. Acids Res. 15:8693–8711, 1987; Skuzeski et. al., Plant Mol. Biol. 15:65–79, 1990).

Optional components of the construct include a marker gene, such as for example, a dominant herbicide resistance gene. Other examples of suitable marker genes include the bar gene which codes for phosphinothricin acetyl transferase.

Optionally, the DNA may include partial T-DNA border sequences, typically retained on integrated DNA following a T-DNA insertion event. Alternately, the integrated exogenous DNA may show some truncation of the left end of the T-DNA, or occasionally, of some DNA beyond the left border, as has been observed after transformation with Agrobacterium.

The construct (i.e., anthocyanin regulatory gene plus promoter) may be cloned into a vector, such as for example, a plasmid. Vectors suitable for transforming plant cells include, but are not limited to, Ti plasmids from *Agrobacterium tumefaciens* (J. Darnell, H. F. Lodish and D. Baltimore, Molecular Cell Biology, 2nd edition, Scientific American Books, N.Y. (1990)), a plasmid containing a β-glucuronidase gene and a cauliflower mosaic virus (CaMV) promoter plus a leader sequence from alfalfa mosaic virus (Sanford et. al., Plant Mol. Biol. 22:751–765, 1993) or a plasmid containing a bar gene cloned downstream from a CaMV 35S promoter and a tobacco mosaic virus (TMV) leader. Other plasmids may additionally contain introns, such as that derived from alcohol dehydrogenase (Adh1), or other DNA sequences. The size of the vector is not a limiting factor.

Transformation of Grasses with the Transgene

The transgenic grass plant may be derived from any number of turfgrasses, including Tall fescue, Kentucky bluegrass, Perennial ryegrass, Creeping bentgrass, Bermuda grass, and Zoysia grass.

Any type or source of plant cells which can serve as a target for transformation by any one or more of the various biological and non-biological delivery mechanisms available in the art can also serve as a target for transformation according to the present invention. This includes, but is not necessarily limited to, immature and mature embryos, pollen, protoplasts, suspension culture cells, callus cells, cotyledon or other seed and seedling parts, leaves or leaf pieces, and roots or root pieces.

Methods of Transfecting the Plant

Delivery or introduction of the DNA construct into eukaryotic cells (i.e., transformation), such as the host plant cells, may be accomplished by a variety of techniques available in the art. Such techniques include non-biological mechanisms such as microprojectile bombardment, electroporation, microinjection, induced uptake, and aerosol beam injection, as well as biological methods such as direct DNA uptake, liposomes and Agrobacterium-mediated transformation. See, for example, Bilang, et. al., Gene 100:247–250, 1991; Scheid et. al., Mol. Gen. Genet. 228:104–112, 1991; Guerche et. al., Plant Science 52:111–116, 1987; Neuhause et. al., Theor. Appl Genet. 75:30–36, 1987; Klein et. al., Nature 327:70–73 1987; Howell et. al., Science 208:1265, 1980; Horsch et. al., Science 227:1229–1231, 1985; DeBlock et. al., Plant Physiology 91:694–701, 1989; Methods for Plant Molecular Biology, Weissbach and Weissbach, eds., Academic Press, Inc., 1988; and Methods in Plant Molecular Biology, Schuler and Zielinski, eds., Academic Press, Inc., 1989. See also, U.S. Pat. Nos. 4,945,050; 5,036,006; and 5,100,792, all to Sanford et. al. Combinations of the above methods may also be used.

Transformation of grass host cells, preferably, is achieved using microprojectile bombardment. As used herein "microprojectile bombardment" is used to refer to the general method of delivering nucleic acids, including DNA and RNA, to a living cell by coating or precipitating the nucleic acids onto a microprojectile, preferably gold particles, and propelling the coated microprojectile into the living cell (see e.g., U.S. Pat. No. 5,036,006 issued Jul. 30, 1991 to Sanford et. al.; U.S. Pat. No. 5,302,523, issued Apr. 12, 1994 to Coffee; Vasil et. al., Biotechnology 11:1553–1558, 1993; and Weeks et. al., Plant Physiol. 102:1077–1084, 1993).

The exact amount of the construct provided to the host cell is not critical and may vary depending on the manner and form in which the component is delivered. If desired, the skilled artisan may routinely vary the amount of construct delivered to determine the optimum level for each using a particular delivery system.

The successful delivery of the DNA into the host cell may be preliminarily evaluated by the transient expression of a "reporter" gene. A reporter gene is a component on the DNA construct introduced into the cell, or a component of a separate DNA construct which is co-introduced into the cell along with the DNA construct comprising the transgene. The property conferred on the transformed cell or tissue by the introduction of the reporter gene is usually easily detectable (e.g., expression of an easily assayable enzyme). "Transient expression" denotes the expression, often cytoplasmic, of a gene before the gene has been stably integrated into the genome of the treated cells or tissue. For example, commonly used reporter genes are the genes coding for the production of chloramphenicol acetyltransferase, which confers resistance to the antibiotic chloramphenicol, or the $E.coli$ β-glucuronidase gene (gusA), the products of which can be detected by a histochemical assay.

Cells that express reporter genes in transient assays may not give rise to cells where the transformed DNA becomes stably integrated into the host cell genome. Selection of cells that express various marker genes, however, does give rise to cells in which the transformed DNA is stably integrated into the host cell genome. Herein, "selection" means conditions where only cells into which the DNA construct has been delivered will grow and cells in which the DNA construct has not been delivered will not grow. For example, cells stably expressing an introduced neomycin phosphotransferase gene are selected by growth in the drug G418, and cells stably expressing the Bar gene are resistant to the herbicide BASTA. Cells stably expressing an introduced drug resistance gene are selected by growth in the presence of the drug. Shoots or plantlets growing in the presence of the drug or herbicide are presumptively transformed. Confirmation of stable integration of the transformed genes into the genome of the host may later be accomplished by, for example, herbicide treatment of the resulting plants. In addition, later molecular detection of the introduced DNA in the isolated genomic DNA of the plant cells, for example using Southern blotting/hybridization or polymerase chain reaction, may be used to confirm integration of the introduced genes into the genome of the host.

Transformed plant host cells are used to regenerate grass plants. In plants, every cell is capable of regenerating into a mature plant and, in addition, contributing to the germ line such that subsequent generations of the plant will contain the transgene. Growth of grass cells and regeneration of the cells into mature plants is common among those skilled in the art.

The transgenic plants are then grown and pollinated with either the same transformed strain or with different strains, and the resulting hybrid, having the desired phenotypic characteristic, is identified. Two or more generations may be grown to ensure that the desired phenotypic characteristic is stably maintained and inherited and then seeds harvested. Transformed progeny obtained by this method may be distinguished from non-transformed progeny by the presence of the introduced gene(s) and/or accompanying DNA (genotype), or the phenotype conferred. Preferably, transformation of the grass is determined by assaying for expression of the anthocyanin gene pigment. Accumulation of anthocyanins is verified by extracting a small piece of blade tissue with acid methanol and measuring the absorbance of the extract at or around 530 nanometers using a spectrophotometer. Alternatively, the color change may be apparent after visual inspection of the plant.

It is contemplated that transgenic plants having a genome comprising a stress inducible promoter operably linked to one or more anthocyanin regulatory genes, will produce anthocyanin pigments prior to development of any lesion or other stress-related phenotype. Advantageously, this will allow actions, such as application of a pesticide, fertilizer, or water, to be taken before the plant or tissue is irreversibly damaged.

The present invention also encompasses transgenic grasses which constitutively express the anthocyanin color gene product. Such grasses comprise, within their genome, an anthocyanin regulatory gene operably linked to a constitutive promoter. Grasses resulting from expression of a transgene under control of a constitutive promoter are used for decorative purposes.

Applicants have observed that overexpression of maize C1/R genes produces grass plants that are red in color. Since anthocyanins produce colors other than red in plants, overexpression of other exogenous anthocyanin regulatory genes may produce transgenic grass plants which exhibit a color other than red, that is different from the color exhibited by non-transgenic plants. Alternatively, to produce grass plants which exhibit a color other than green or red, the transgenic grass is co-transformed with a transgene comprising a sequence which encodes an exogenous anthocyanin biosynthesis gene, such as for example the cyt b5 gene whose gene product confers blue colors to flowers. (Proc. Natl. Acad. Sci. USA Vol. 96, pp 778–783. January, 1999)

EXAMPLES

The following examples are for purposes of illustration only and are not intended to limit the scope of the invention as defined in the claims which are appended hereto. The references cited in this document are specifically incorporated herein by reference.

Example 1

DNA constructs comprising the CMV 35 S promoter, operably linked to the R gene from maize, the C1 gene from maize, and the reporter gene β-glucuronidase, were prepared using standard recombinant DNA techniques. All constructs were introduced into leaf sheaths of Tall fescue via particle bombardment with gold particles using a DuPont Biolistic particle delivery system. After bombardment, cells were transferred to fresh medium. Anthocyanin accumulation was observed in leaf sheaths and roots after 48 hours.

Example 2

Kentucky bluegrass immature embryos (embryonic calli) are transformed with DNA constructs comprising the CMV 35 S promoter, operably linked to the R gene from maize, the C1 gene from maize, and the reporter gene β-glucuronidase via particle gun bombardment as described above in Example 1. The transformed plant embryo cells are used to generate transgenic grass plants. This is done by mechanically dispersing the transformed cells, such that single cell clones are obtained, and then growing the clones in medium plus the appropriate hormones such that transgenic grass plants develop. Anthocyanin accumulation is either visually observed in the blades of the transgenic grass plant or is detected spectrophotometrically following extraction of anthocyanin from the blade using methanol or both.

Example 3

Perennial ryegrass is transfected with DNA constructs comprising the CMV 35 S promoter operably linked to the R gene from maize, the C1 gene from maize, and the reporter gene β-glucuronidase, via particle gun bombardment, as described above in Example 1. The transgenic plant cells are used to generate transgenic grass plants and anthocyanin expression is observed in the plants as described above in Example 2.

Example 4

Promoter sequences from the rab28 gene are generated by PCR and cloned into a construct comprising the C1/R chimeric regulatory gene. A vector is constructed such that the regulatory gene encoding C1/R is downstream from, and regulated by, the rab28 promoter. The resulting vector is introduced into embryogenic calli suspension cultures of Kentucky bluegrass, Perennial ryegrass or Tall fescue, via particle bombardment. A bialaphos herbicide resistance selectable marker, under the control of a 35 S promoter, is simultaneously introduced into the cells of the cultures. Calli resistant to the herbicide are selected and maintained before transferring to the regeneration medium, from which plantlets are selected. Transformed pantalets are selected, and anthocyanin pigmentation detected under different light intensities before and after treatment with absicic acid, which mimics the drought inducibility of the rab28 promoter.

What is claimed is:

1. A transgenic grass plant whose color phenotype changes to signal its exposure to a chemical or stress conditions, the transgenic grass plant comprising a transgene comprising:
   a) an exogenous anthocyanin regulatory gene; and
   b) an inducible promoter for regulating transcription of said anthocyanin regulatory gene, said promoter being operably linked to said anthocyanin regulatory gene,
   wherein the promoter is induced when the transgenic grass plant is exposed to a chemical or stress conditions, and wherein a change in color phenotype of the transgenic grass plant signals response of the transgenic grass plant to a chemical or stress conditions.

2. The transgenic grass plant of claim 1 wherein the promoter is a stress inducible promoter.

3. The transgenic grass plant of claim 2 wherein the stress inducible promoter is responsive to lack of fertilizer, lack of water, or infection with a pathogen.

4. The transgenic grass plant of claim 1 wherein the promoter is selected from the group consisting of the maize rab28 gene promoter, the maize rab17 gene promoter, the maize Ivr2 gene promoter, and the hydroxyproline-rich glycoprotein gene promoter.

5. The transgenic grass plant of claim 1 wherein the promoter is a chemical inducible promoter.

6. The transgenic grass plant of claim 1 wherein the chemical inducible promoter is responsive to a steroid or estradiol.

7. The transgenic grass plant of claim 1 wherein the grass is a turfgrass.

8. The transgenic grass plant of claim 1 wherein the turfgrass is selected from the group consisting of Tall fescue, Kentucky bluegrass, Perennial ryegrass, Creeping bentgrass, Bermuda grass, and Zoysia grass.

9. The transgenic grass plant of claim 1 wherein the anthocyanin regulatory gene is selected from the group consisting of a maize R gene, a combination of a maize C1 gene and a maize R gene, and a DNA construct encoding a chimeric CRC protein.

10. A nucleic acid construct comprising:
    a) an anthocyanin regulatory gene selected from the group consisting of an R gene, a combinations of a C1 gene and an R gene, and a DNA construct encoding chimeric CRC protein; and
    b) a stress inducible promoter operably linked to the anthocyanin regulatory gene, wherein the stress inducible promoter is responsive to stress conditions selected from the group consisting of lack of fertilizer, lack of water, and infection with a pathogen.

11. The nucleic acid construct of claim 10, wherein the inducible promoter is selected from the group consisting of the maize rab28 gene promoter, the maize rab17 gene promoter, to maize Ivr2 gene promoter, and the hydroxyproline-rich glycoprotein gene promoter.

12. The nucleic acid construct of claim 10, further comprising one or more of the sequences selected from the group consisting of a leader sequence, intron sequence, transcription terminator, and a polyadenylation site.

13. The nucleic acid construct of claim 10, further comprising one or more of the sequences selected from the group consisting of a marker gene sequence, a selectable gene sequence and a T-DNA sequence.

14. A method for making a transgenic grass plant which exhibits a color change in response to its exposure to a chemical or stress conditions, comprising:
    a) introducing a nucleic acid construct into a plant cell or protoplast, said construct comprising
       i.) an exogenous anthocyanin regulatory gene; and
       ii.) an inducible promoter for regulating transcription of said anthocyanin regulatory gene, said promoter being operably linked to said anthocyanin regulatory gene,
    b) regenerating a transgenic grass plant from said plant cell or protoplast containing said nucleic acid construct, and
    c) exposing the transgenic grass plant to a chemical or stress condition,
    wherein said chemical or stress condition induces said promoter, and causes a change in color of the transgenic grass plant, which signals the response of the transgenic grass plant to said chemical or stress conditions.

15. The method of claim 14 wherein the plant cell used for introduction of the nucleic acid construct is from a grass plant selected from the group consisting of Tall fescue, Kentucky bluegrass, Perennial ryegrass, Creeping bentgrass, Bermuda grass and Zoysia grass.

16. The method of claim 14 wherein the promoter is selected from the group consisting of a stress inducible promoter and a chemical inducible promoter.

17. A seed of any generation of the transgenic grass plant of claim 1, wherein said seed comprises said transgene.

18. The method of claim 14, wherein the nucleic acid construct further comprises a sequence selected from the group consisting of a leader sequence, intron sequence, transcription terminator, polyadenylation site, and combinations thereof.

19. The method of claim 14, wherein the nucleic acid construct further comprises a marker gene sequence, a selectable gene sequence, T-DNA sequence, or combinations thereof.

20. The method of claim 14, wherein said anthocyanin regulatory gene is selected from the group consisting of an R gene, a combination of a C1 gene and an R gene, and a DNA construct encoding a chimeric CRC protein.

* * * * *

UNITED STATES PATENT AND TRADEMARK OFFICE
CERTIFICATE OF CORRECTION

PATENT NO. : 6,709,867 B2
DATED : March 23, 2004
INVENTOR(S) : Erich Grotewold

It is certified that error appears in the above-identified patent and that said Letters Patent is hereby corrected as shown below:

Title page,
Item [57], ABSTRACT,
Line 3, please insert -- . -- following "provided"

Column 9,
Line 19, please delete "pantalets" and insert -- plantlets --
Line 67, please delete "combinations" and insert -- combination --

Column 10,
Line 12, please delete "to" and insert -- the --

Signed and Sealed this

Nineteenth Day of April, 2005

JON W. DUDAS
*Director of the United States Patent and Trademark Office*